US011298495B1

United States Patent
Robinson (10) Patent No.: US 11,298,495 B1
(45) Date of Patent: Apr. 12, 2022

(54) PERSONAL PROTECTIVE EQUIPMENT AND PATHOGEN CONTAINMENT SYSTEM FOR ORAL AND DENTAL PROCEDURES

(71) Applicant: Keith Alan Robinson, Katy, TX (US)

(72) Inventor: Keith Alan Robinson, Katy, TX (US)

( * ) Notice: Subject to any disclaimer, the term of this patent is extended or adjusted under 35 U.S.C. 154(b) by 0 days.

(21) Appl. No.: 17/468,967

(22) Filed: Sep. 8, 2021

Related U.S. Application Data (63) Continuation of application No. 17/031,289, filed on Sep. 24, 2020.

(51) Int. Cl.
*A61M 16/00* (2006.01)
*A61M 16/06* (2006.01)

(52) U.S. Cl.
CPC .... *A61M 16/0666* (2013.01); *A61M 16/0688* (2014.02); *A61M 16/0694* (2014.02); *A61M 2202/0466* (2013.01); *A61M 2202/203* (2013.01); *A61M 2202/206* (2013.01); *A61M 2210/0618* (2013.01); *A61M 2210/0625* (2013.01)

(58) Field of Classification Search
CPC .......... A61M 16/0666; A61M 16/0688; A61M 16/0694; A61M 2202/0466; A61M 2202/203; A61M 2202/206; A61M 2210/0618; A61M 2210/0625
See application file for complete search history.

(56) References Cited

U.S. PATENT DOCUMENTS

| | | | | |
|---|---|---|---|---|
| 4,895,172 | A * | 1/1990 | Lindkvist | A61M 16/0694 128/863 |
| 5,127,411 | A * | 7/1992 | Schoolman | A61B 90/40 128/863 |
| 7,481,217 | B2 * | 1/2009 | Milles | A61M 16/009 128/205.12 |
| 2008/0276941 | A1 * | 11/2008 | Doty | A61M 16/009 128/205.28 |
| 2020/0376213 | A1 * | 12/2020 | He | A61M 16/0009 |

\* cited by examiner

*Primary Examiner* — Steven O Douglas
(74) *Attorney, Agent, or Firm* — The Rapacke Law Group P.A.

(57) ABSTRACT

A pathogen containment system for use during healthcare procedures is disclosed, comprising a flexible tubing dimensioned to extend around a user's mouth, the flexible tubing including a first end and a second end. A connector includes a central portion including a first side fittingly engaged with the first end of the flexible tubing and a second side fittingly engaged with the second end of the flexible tubing. An attachment port is positioned perpendicular to the central portion, the attachment port is in fluid communication via a vacuum tubing to a vacuum suction unit. A plurality of intake ports are provided on the flexible tubing to permit air to be drawn therethrough via the vacuum suction unit. The air intake ports capture a contaminant emitted from the user's mouth or the user's nose.

20 Claims, 8 Drawing Sheets

PERSONAL PROTECTIVE EQUIPMENT AND PATHOGEN CONTAINMENT SYSTEM FOR ORAL AND DENTAL PROCEDURES

CROSS-REFERENCE TO RELATED APPLICATIONS

The present application is a Continuation Patent Applications and claims priority to U.S. Non-Provisional patent application Ser. No. 17/031,289 filed Sep. 24, 2020, entitled "PERSONAL PROTECTIVE EQUIPMENT AND PATHOGEN CONTAINMENT SYSTEM FOR ORAL AND DENTAL PROCEDURES," which is hereby incorporated by reference in its entirety.

TECHNICAL FIELD

The embodiments generally relate to personal protective equipment and, more specifically, to personal protective equipment to aid in the containment of pathogens during a dental or oral procedure.

BACKGROUND

Viral and bacterial pathogens such as COVID-19, influenza, and the like can be quickly spread from an infected human carrier (host) to many people (recipients) via aerosols and/or droplets of moisture emitted from the mouth, nose, throat, or aerodigestive tract of the host. Transmission can occur from asymptomatic and symptomatic hosts, making the identification of those who are affected and the preventative containment of the pathogens difficult if not impossible.

One approach to minimizing the likelihood of spreading these pathogens is to prevent/minimize the cloud formation of aerosols and droplets that is emitted from the host. In such, the use of masks has been cited as a primary means for reducing the propensity of the pathogens to spread from the mouth, nose, throat, or aerodigestive tract of the host. While effective when properly worn and constructed of appropriately tested materials, masks block the mouth and nose of the user and must be removed during dental and oral procedures, leaving the dentist, hygienist, physician, or other medical professional exposed to direct bombardment of pathogens and increased risk of infection by the host during a procedure.

In the current arts, healthcare facilities may utilize UV light units mounted on the ceilings or walls of rooms, as well as on some functional equipment, to sterilize the surrounding environment. Further, some facilities utilize suction devices placed at a distance from the potentially infected individual to create a distant suction and negative pressure to pull the airborne contaminants from circulation in the air. Because these implements operate at a distance from the host while allowing pathogens to circulate in the air before their neutralization or collection in a suction unit, the pathogens may still contact and infect non-infected individuals in the environment. In the case of remote suction units, the suction may actually draw the pathogens towards a potential recipient, thus increasing the likelihood of disease transmission.

SUMMARY OF THE INVENTION

This summary is provided to introduce a variety of concepts in a simplified form that is further disclosed in the detailed description of the embodiments. This summary is not intended to identify key or essential inventive concepts of the claimed subject matter, nor is it intended for determining the scope of the claimed subject matter.

The embodiments described herein provide a pathogen containment system for use during healthcare procedures, the system comprising a flexible tubing dimensioned to extend around a user's mouth, the flexible tubing including a first end and a second end. A connector includes a central portion including a first side fittingly engaged with the first end of the flexible tubing and a second side fittingly engaged with the second end of the flexible tubing. An attachment port is positioned perpendicular to the central portion, the attachment port is in fluid communication via a vacuum tubing to a vacuum suction unit. A plurality of intake ports are provided on the flexible tubing to permit air to be drawn therethrough via the vacuum suction unit. The air intake ports capture a contaminant emitted from the user's mouth or the user's nose.

The device is an easy-to-use personal protective equipment (PPE) that is disposable and designed to capture airborne contaminants as close to the site of origin (i.e., the user's mouth and/or nose) as possible while forcibly transporting the contaminants away from the host and potential recipients. The device allows for healthcare professionals to perform procedures (including diagnostic and treatment procedures) in and around the mouth, nose, throat, nasopharynx, and/or aerodigestive tract of the host while preventing the emission of pathogens and the creation of a cloud of airborne particles which may contaminate the healthcare professional. The device provides an active means for capturing pathogens and other contaminants in both infected and potentially infected individuals.

In one aspect, at least one pad is positioned on a back side of the flexible tubing.

In one aspect, the at least one pad includes an adhesive to adhere the pad to the user's skin.

In one aspect, a strap includes a first end having a first retainer and a second end having a second retainer each attached to the flexible tubing, wherein the strap extends around the user's head.

In one aspect, a saliva ejection port is positioned on the connector. Specifically, the saliva ejection port is positioned on an opposing side of the attachment port.

In one aspect, a plug is tethered to the saliva ejection port to cover the saliva ejection port.

In one aspect, a saliva ejector is attached to the saliva ejection port to extend into the user's mouth to capture saliva, or, when the lips are pursed around the suction activated saliva ejector, will force expired air generated by a user's cough or sneeze, directing aerodigestive generated droplets directly into the device to be carried away from user and nearby healthcare personnel.

BRIEF DESCRIPTION OF THE DRAWINGS

A complete understanding of the present embodiments and the advantages and features thereof will be more readily understood by reference to the following detailed description when considered in conjunction with the accompanying drawings wherein.

DETAILED DESCRIPTION

The specific details of the single embodiment or variety of embodiments described herein are to the described apparatus. Any specific details of the embodiments are used for demonstration purposes only, and no unnecessary limitations or inferences are to be understood therefrom.

Before describing in detail exemplary embodiments, it is noted that the embodiments reside primarily in combinations of components and procedures related to the apparatus. Accordingly, the apparatus components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

The specific details of the single embodiment or variety of embodiments described herein are set forth in this application. Any specific details of the embodiments are used for demonstration purposes only, and no unnecessary limitation or inferences are to be understood therefrom. Furthermore, as used herein, relational terms, such as "first" and "second," "top" and "bottom," and the like, may be used solely to distinguish one entity or element from another entity or element without necessarily requiring or implying any physical or logical relationship, or order between such entities or elements.

The device has been developed as an easy-to-use personal protective equipment (PPE) that is disposable and designed to capture airborne contaminants as close to the site of origin (i.e., the user's mouth and/or nose) as possible while forcibly transporting the contaminants away from the host and potential recipients. The device allows for healthcare professionals to perform procedures (including diagnostic and treatment procedures) in and around the mouth, nose, throat, nasopharynx, and/or aerodigestive tract of the host while preventing the emission of pathogens and the creation of a cloud of airborne particles which may contaminate the healthcare professional.

The embodiments provide a device which begins the collection and removal of pathogens at or near the site of origination and before the pathogens reach potential recipients. The device is provided as a single-use disposable unit, which can be applied to the patient (potential host) before undergoing a procedure at a healthcare facility. The device may be blister packaged and sterilized and packaged to prevent cross-contamination during manufacturing, shipping, transporting, and storing of the device. The device may be made in various sizes to accommodate various applications including the size of the wearer (e.g., sizes for adults, children, men, women, etc.) as well as being readily applicable to non-human sources of contamination, such as toilets, etc.

The device may be used in a variety of settings, such as by healthcare professionals, dental professionals and used by dentists, dental assistants, hygienists, oral pathologists, prosthodontists, oral surgeons, periodontists, and implantologists among other professionals who work in, around or through the mouth, nose, lips or facial areas. The device may be used preventatively on potentially infected patients entering a confined area wherein the pathogen is more likely to spread.

Many pathogens, including the sever acute respiratory syndrome coronavirus 2 (SARS-CoV-2) can be catapulted into the atmosphere surrounding a carrier by normal human behaviors such as speaking, exhaling, coughing, or sneezing. A single sneeze can contain upwards of 40,000 micro-droplets which are projected up t a distance of 27 feet. Many similar pathogens are carried through the air on micro-droplets and/or aerosols, which can remain suspended in the air for extended periods of time depending on atmospheric conditions (e.g., convection air currents, wind currents, air temperature, humidity, dryness, and other factors). Once airborne, these pathogens may remain suspended in the air and/or land on a surface where they may remain until inactivated or until transmission to a human host. The greatest velocity experienced by the pathogen during the transmission cycle occurs when exiting the mouth or nose of the host. The device is positioned to capture and/or collect the pathogens as they exit the mouth to limit the likelihood of transmission.

The device may be useful for preventing transmission and/or infection of a plurality of diseases which infect the respiratory system including: chickenpox (varicella), coronavirus infections, diphtheria, group A *streptococcus*, hemophilus influenza type B, influenza, legionnaires' disease, measles, middle east respiratory syndrome, mumps, pneumonia, pneumococcal meningitis, rubella, sever acute respiratory syndrome (SARS), tuberculosis, and whooping cough (pertussis) among others.

In general, the embodiments provided herein relate to a pathogen containment device (hereinafter "the device") utilized as personal protective equipment to actively capture pathogens and the micro-droplets and/or aerosols they are transported on when exiting the mouth of the wearer (i.e., the host) of the device. The device comprises a flexible tubing having a plurality of intake ports to allow air to flow therethrough. A pad is adhered to the flexible tubing and provides a comfortable cushion while the user wears the device around their mouth. The flexible tubing is connected to a suction device to draw air in through the plurality of intake ports and through a connector attaching the flexible tubing to the suction device.

Figure 1:
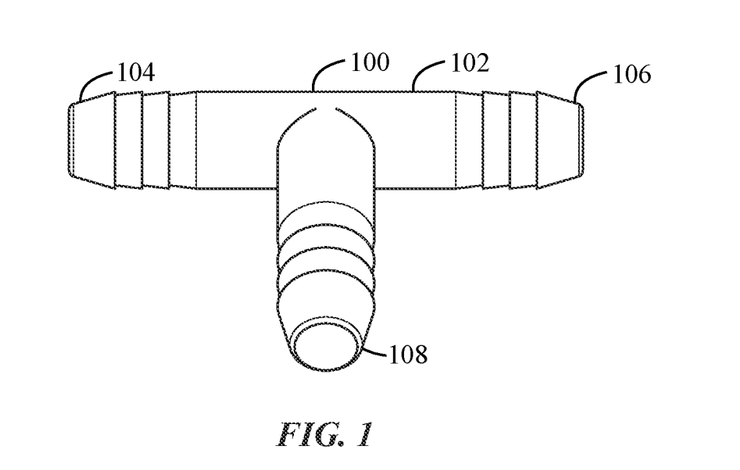
FIG. 1 illustrates a perspective view of the connector, according to some embodiments.

FIG. 1 illustrates a perspective view of the connector 100 having a central portion 102 having a first side 104 and a second side 106, each having an aperture which forms an end-to-end through-hole through the interior of the connector 100. An attachment port 108 extends about perpendicular from the central portion 102 and is provided with an aperture in fluid communication with the end-to-end through-hole of the central portion 102. The attachment port 108 allows for the removeable engagement of a vacuum suction device to draw air through the first side 104 and second side 106 of the connector 100.

Figure 2:
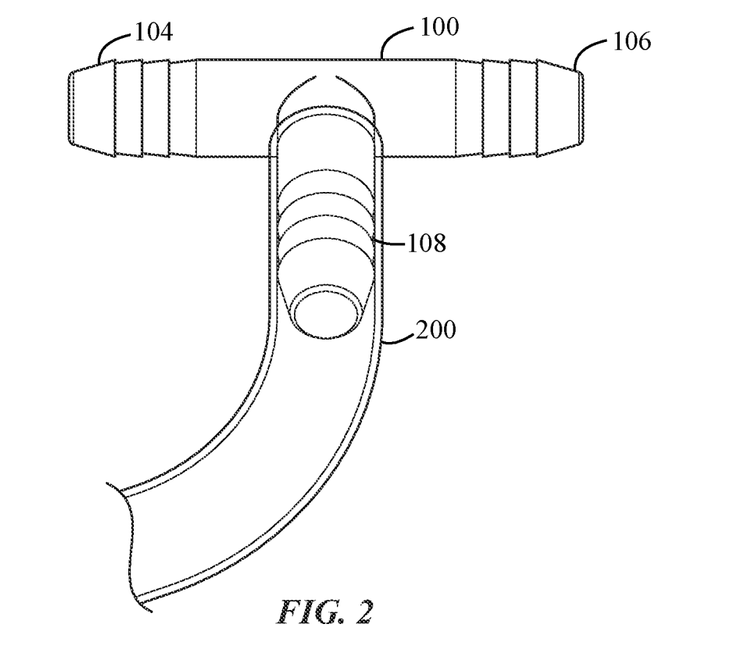
FIG. 2 illustrates a perspective view of the connector and vacuum tubing, according to some embodiments.

FIG. 2 illustrates the connector 100 having a vacuum tubing 200 fittingly engaged to the attachment port 108. The vacuum tubing 200 is in fluid communication with a vacuum suction device to draw air in through the first and second sides 104, 106 of the connector 100. The vacuum tubing is constructed of a material to maintaining full distention during high-speed vacuum provided by the vacuum suction unit. The vacuum tubing may also be constructed to resist excessive bending, which may stop the flow of air and reduce the effectiveness of the device.

Figure 3:
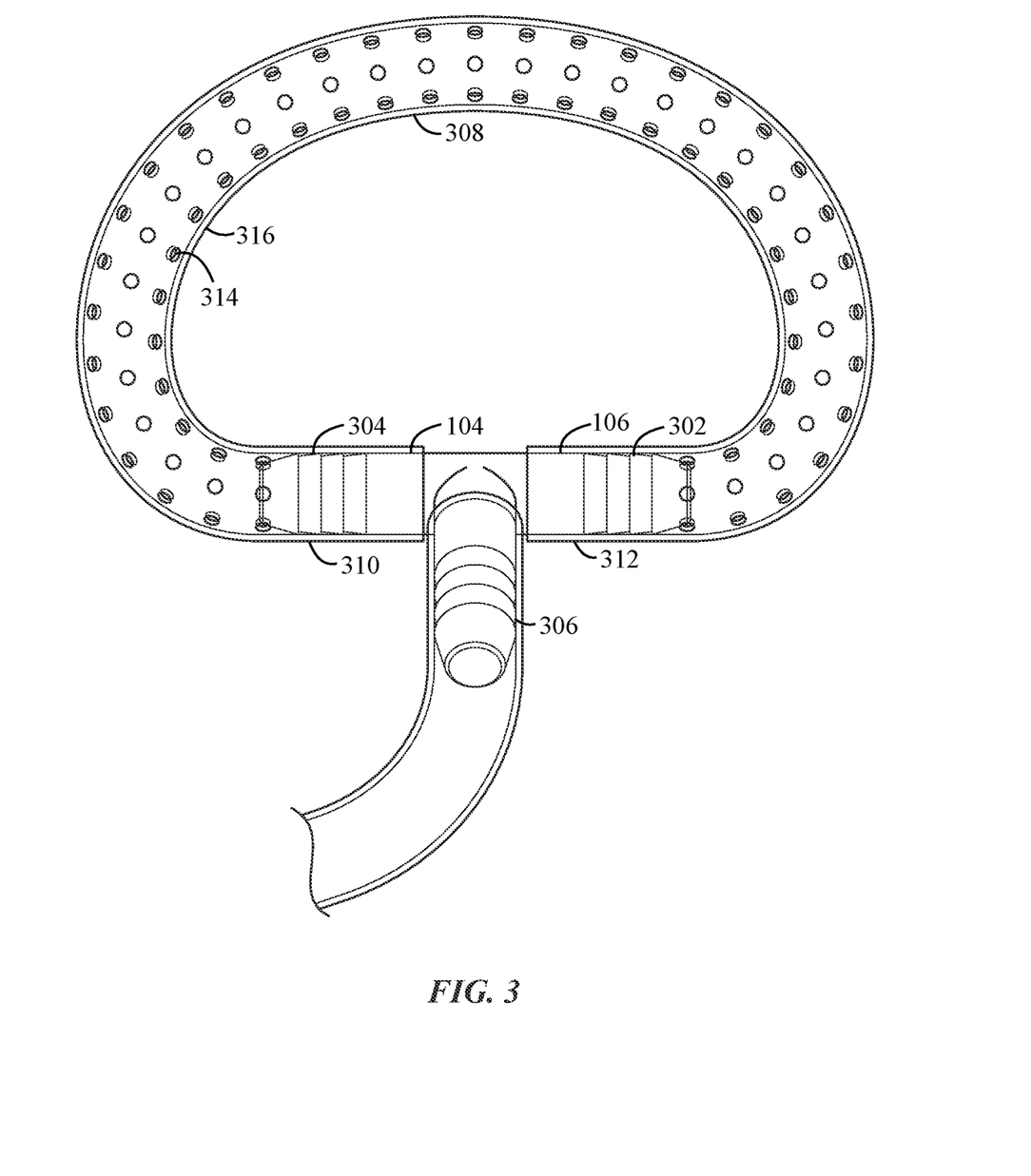
FIG. 3 illustrates a perspective view of the flexible tubing, connector and vacuum tubing, according to some embodiments.

FIG. 3 illustrates the first side 104, second side 106, and attachment port 108 having attachment portions 302, 304, 306 formed as ridges to fittingly engage with the flexible tubing 308. The flexible tubing 308 comprises a first end 310 fittingly engaged to the first side 104 and a second end 312 fittingly engaged to the second side 106 to form a semicircular configuration. The flexible tubing 308 includes a plurality of air intake ports 314 through the sidewall 316 to allow air to flow therethrough, driven via the vacuum suction unit.

Figure 4:
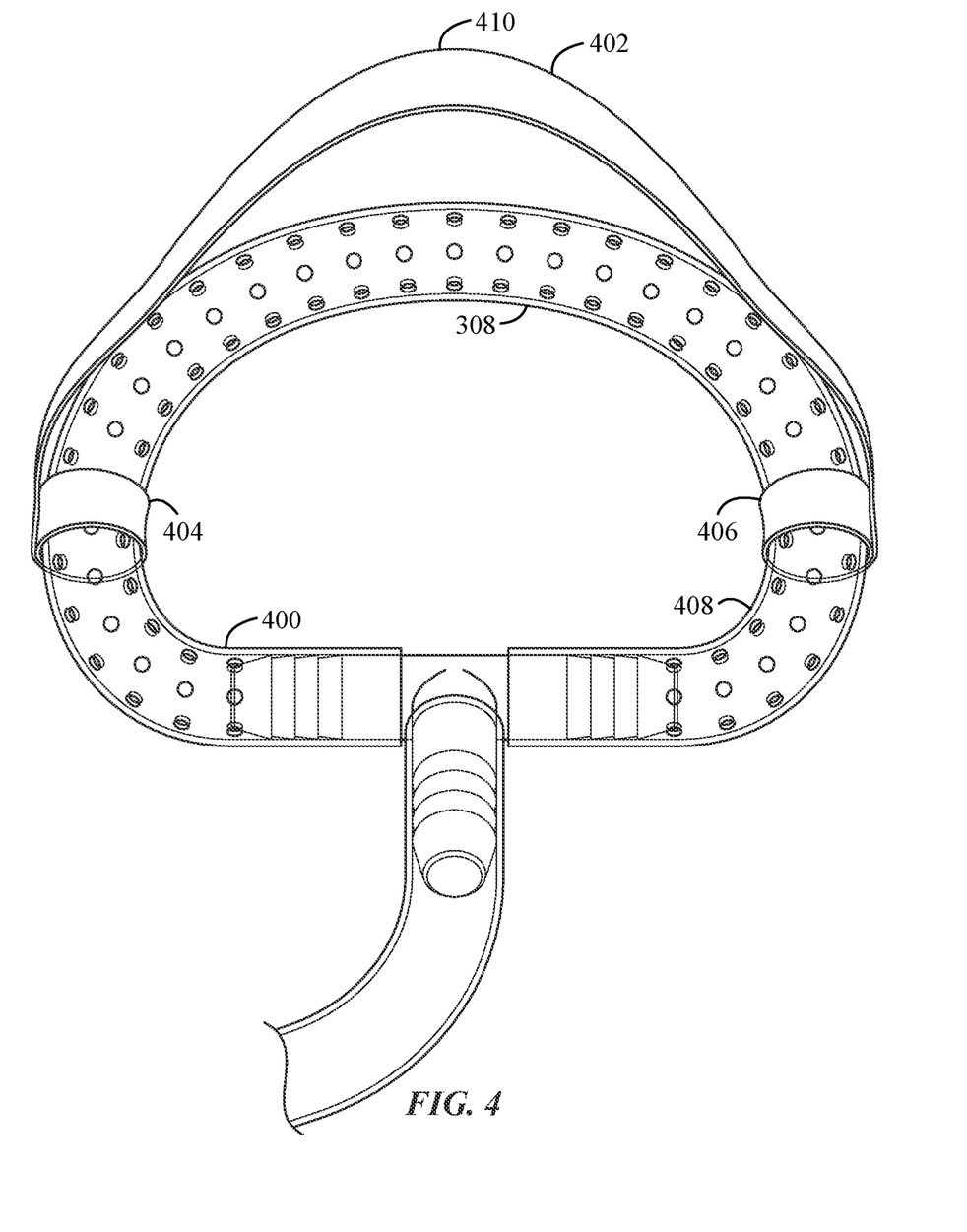
FIG. 4 illustrates a perspective view of the device including the strap connected to the flexible tubing, according to some embodiments.

FIG. 4 illustrates the device 400 including a strap 402 attached to the flexing tubing 308 to retain the device 400 on the face of the user. The strap 402 includes a first retainer 404 and a second retainer 406 positioned at opposing ends of the strap 402 and each extending circumferentially around the outer perimeter 408 of the flexible tubing 308. The strap 402 is dimensioned to fit around the head of the user such that the middle portion 410 of the strap 402 contacts the sides and back of the head of the user during use.

In some embodiments, the strap 402 may be adjustable to fit various head sizes and shapes to accommodate a variety of users including men, women, adults, and children alike. In another embodiment, the strap 402 may be constructed at least partially of an elastic material to allow the strap 402 to stretch around the head of the user.

Figure 5:
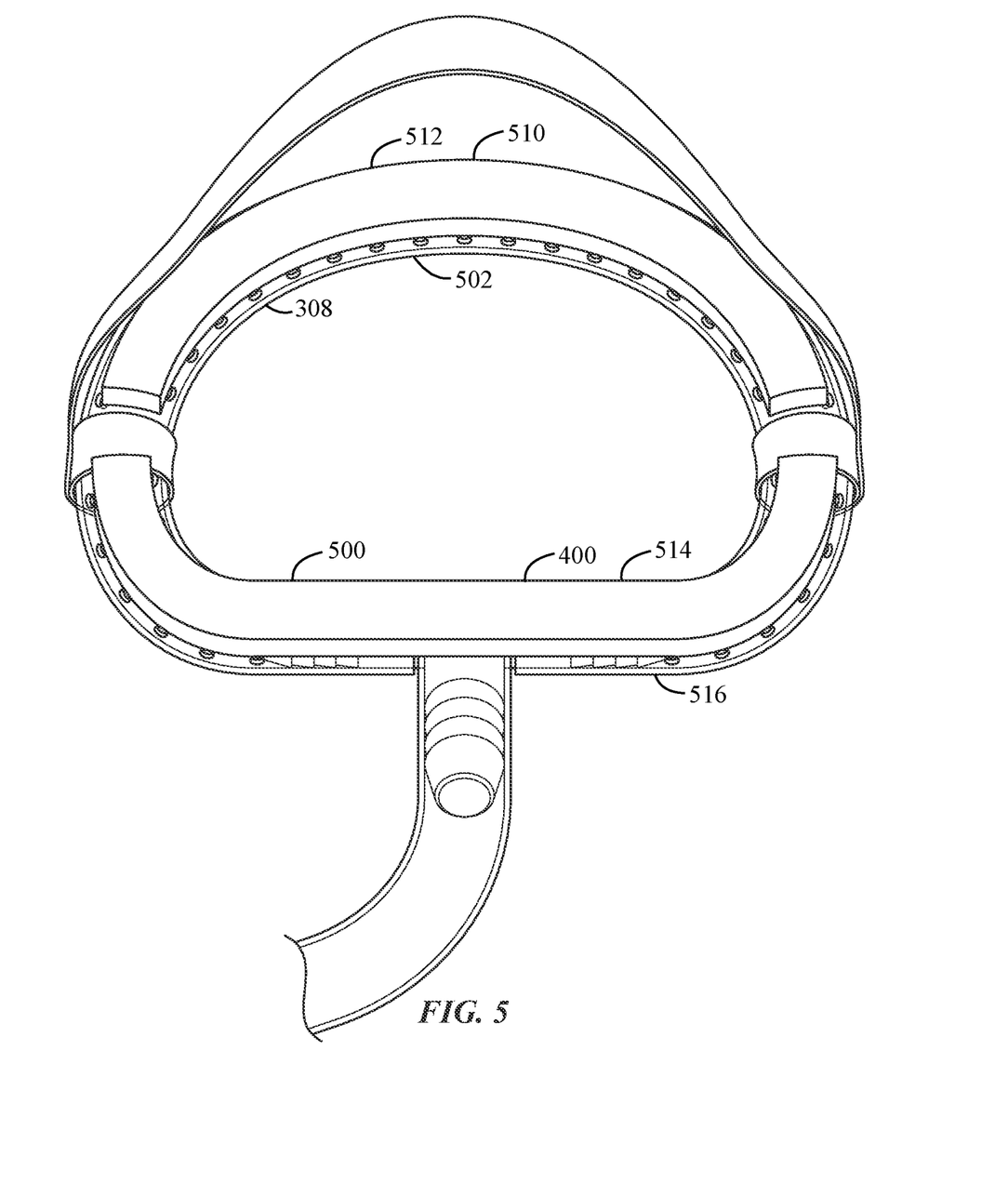
FIG. 5 illustrates a perspective view of the device including the pad(s) and strap, according to some embodiments.
Figure 6:
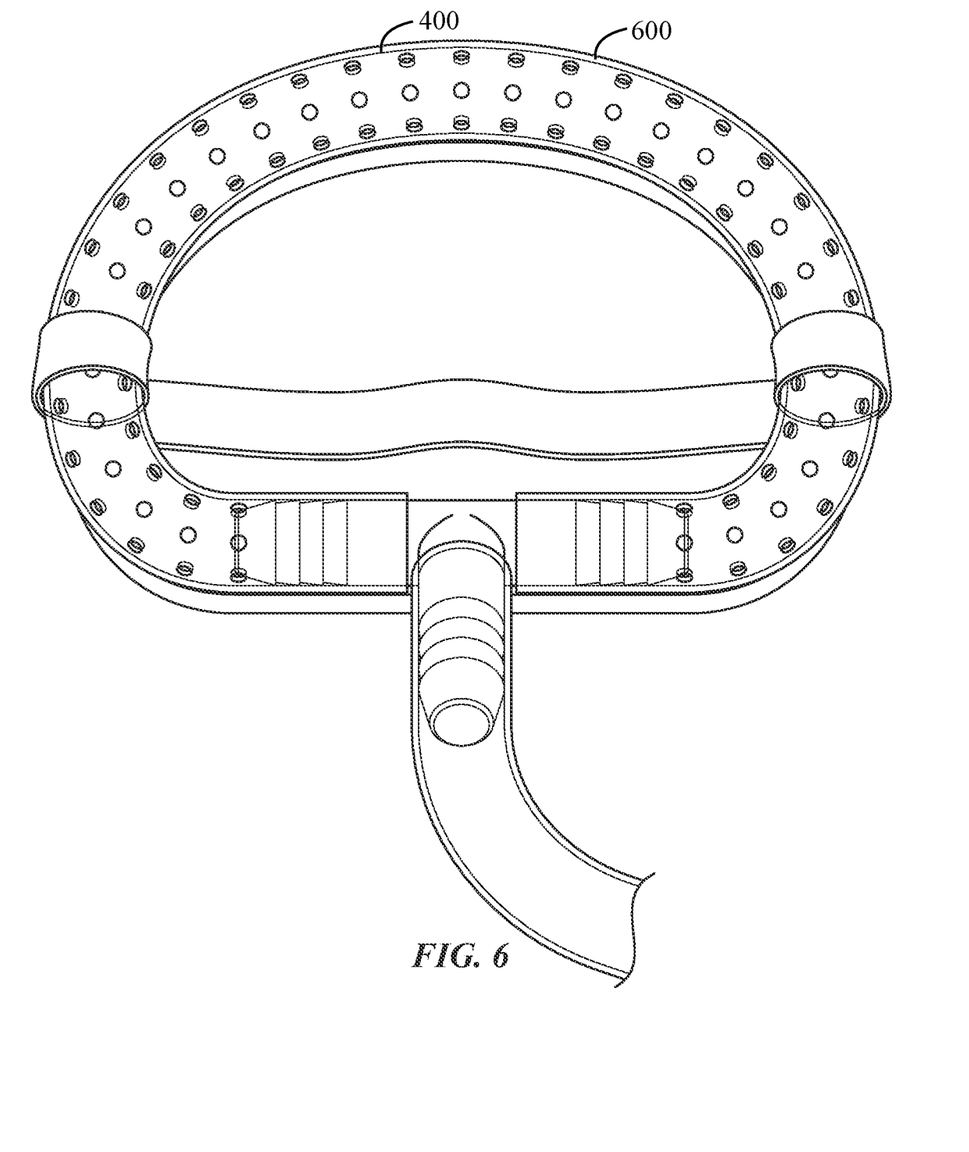
FIG. 6 illustrates a perspective view of the device, according to some embodiments.

FIG. 5 illustrates the device 400 and one or more pads 500 positioned on a back side 502 of the flexible tubing 308. The pad(s) 500 are attached via an adhesive, bonding, or similar means known in the arts such that the pad(s) 500 contact the skin on the user's face during use. The pad(s) 500 are constructed of a resiliently malleable material to provide a cushion and comfort during extended periods of use, while providing a barrier between the flexile tubing 308 and the skin of the user. In such, the pad(s) distance the flexible tubing 308 from the face of the user to strategically position the device in an optimal position for capturing pathogens exiting the mouth of the user. FIG. 6 illustrates the front side 600 of the device 400, wherein the front side 600 is oriented away from the skin of the user during use.

In some embodiments, and in further reference to FIG. 5, the device 400 comprises a first pad 510 arranged at the top 512 of the device 400 and a second pad 514 positioned at the bottom 516 of the device 400. The first retainer 404 and second retainer 406 are positioned between the first pad 510 and second pad 514 to retain the strap 402 in a suitable position.

Figure 7:
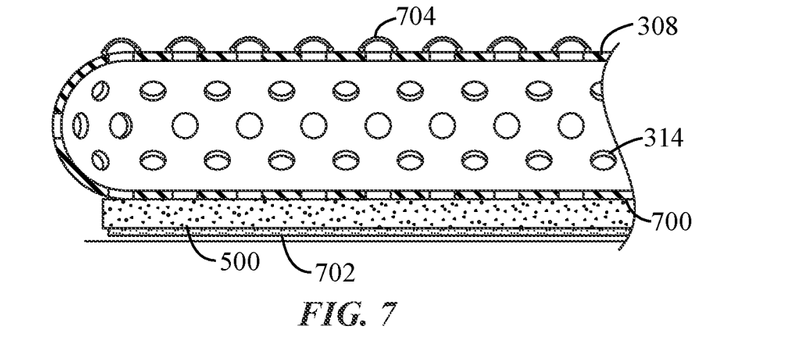
FIG. 7 illustrates a side elevation view of the flexible tubing, pad, and adhesive, according to some embodiments.

FIG. 7 illustrates a side cross-section view of the flexible tubing 308 attached to the pad 500 via an adhesive layer 700. A skin adhesive 702 may be provided on the pad 500 to adhere the pad 500 to the skin of the user and retain the device in a suitable position during use. Each intake port 314 is provided with a distender 704. Each distender 704 may be inserted into each intake port 314 to prevent the malformation of the intake port 314.

Figure 8:
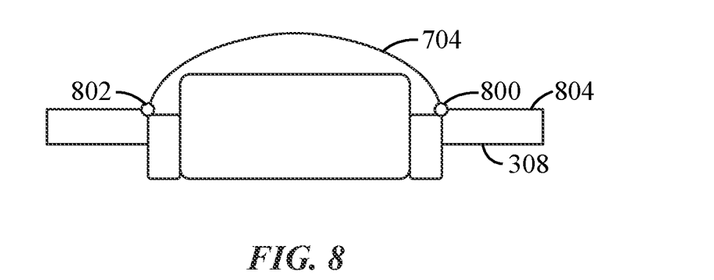
FIG. 8 illustrates a side elevation view of the distender, according to some embodiments.
Figure 9:
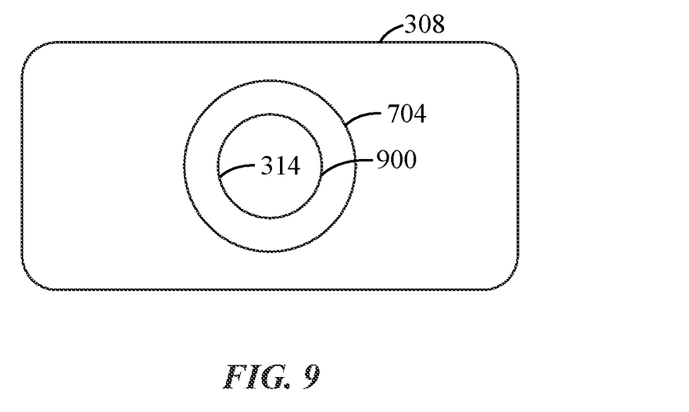
FIG. 9 illustrates a top plan view of the distender, according to some embodiments.

FIG. 8 illustrates a side elevation view of the distender 704 having retention lips 800, 802 to prevent the distender 704 from being drawn through the intake port 314 under vacuum. In such, the retention lips 800, 802 contact the exterior surface 804 of the flexible tubing 308 and prevent the strong vacuum forces from sucking the distender 704 through the air intake ports 314. FIG. 9 illustrates a top plan view of the distender 704 positioned circumferentially around the opening 900 of the intake port 314 such that the distender 704 permits air to flow through the opening without the malformation of the flexible tubing 308 and intake ports 314 thereof under vacuum.

Figure 10:
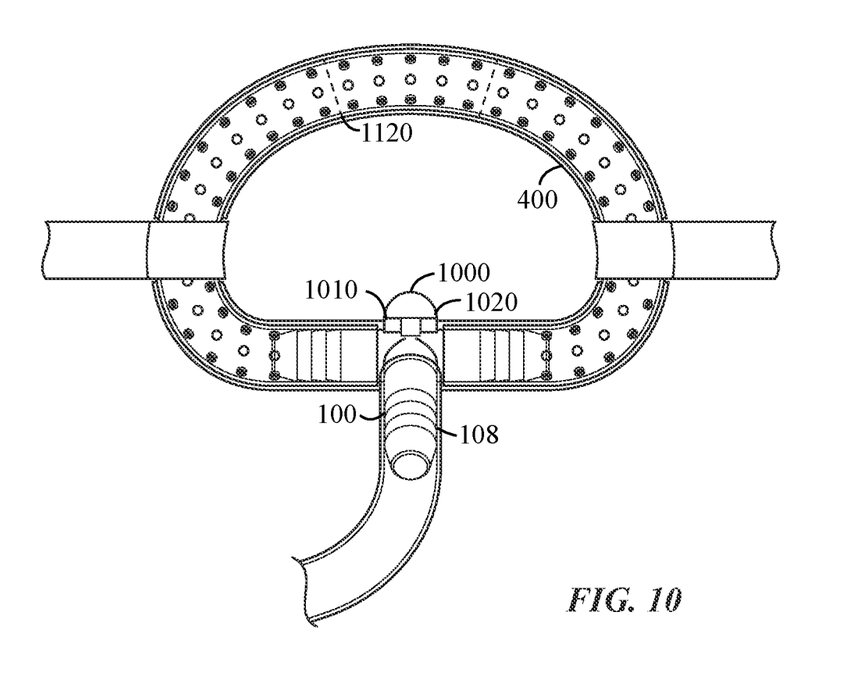
FIG. 10 illustrates a perspective view of the device having a plug positioned on the saliva ejection port, according to some embodiments.

FIG. 10 illustrates the device 400 including a plug 1000 positioned over the saliva ejection port 1010 of the connector 100. The saliva ejection port 1010 is an aperture positioned on the back side 1020 of connector 100 and on an opposite side of the attachment port 108 to allow saliva to exit the patient's mouth and enter the device 400. The plug 1000 covers the aperture and prevents the flow of saliva into the device 400, which may be useful in some applications and procedures.

FIG. 10 further illustrates a nasal target area 1120 which is positioned below the nostrils of the user during use. The nasal target area 1120 may include a cutout and/or mounts to retain the device 400 in a suitable position on the face of the user, while provide comfort during extended periods of use.

In some embodiments the plug 1000 may be tethered to the saliva ejection port 1010.

Figure 11:
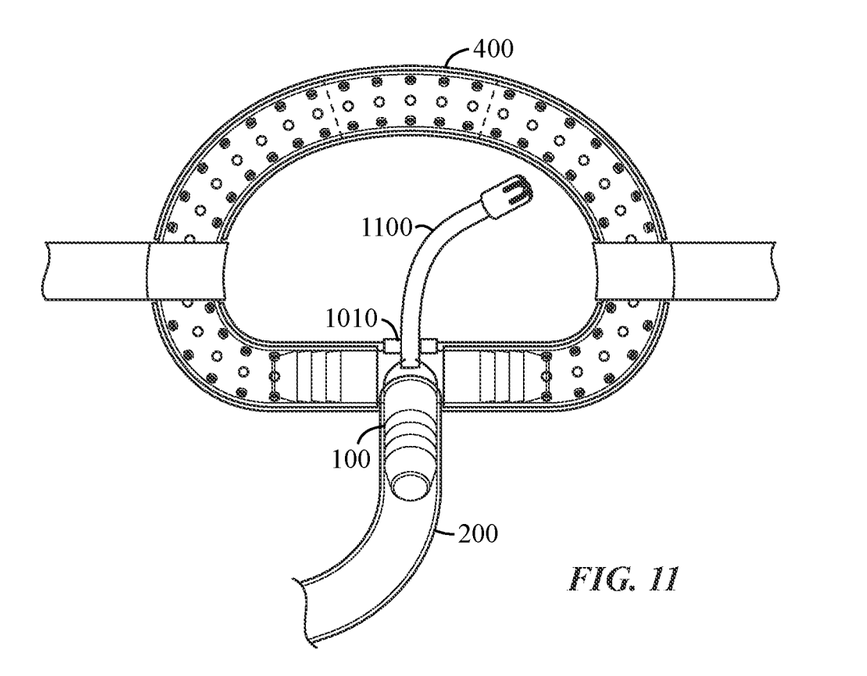
FIG. 11 illustrates a perspective view of the device having a saliva ejector connected to the saliva ejection port, according to some embodiments.

FIG. 11 illustrates the device 400 including a saliva ejector 1100 positioned over the saliva ejection port 1010 of the connector 100. The saliva ejector 1100 is in fluid communication with the vacuum suction device connected to the vacuum tubing 200. During use, the saliva ejector 1100 may be extended into the mouth of the user to provide vacuum suction within the mouth and draw saliva into the device.

Figure 12:
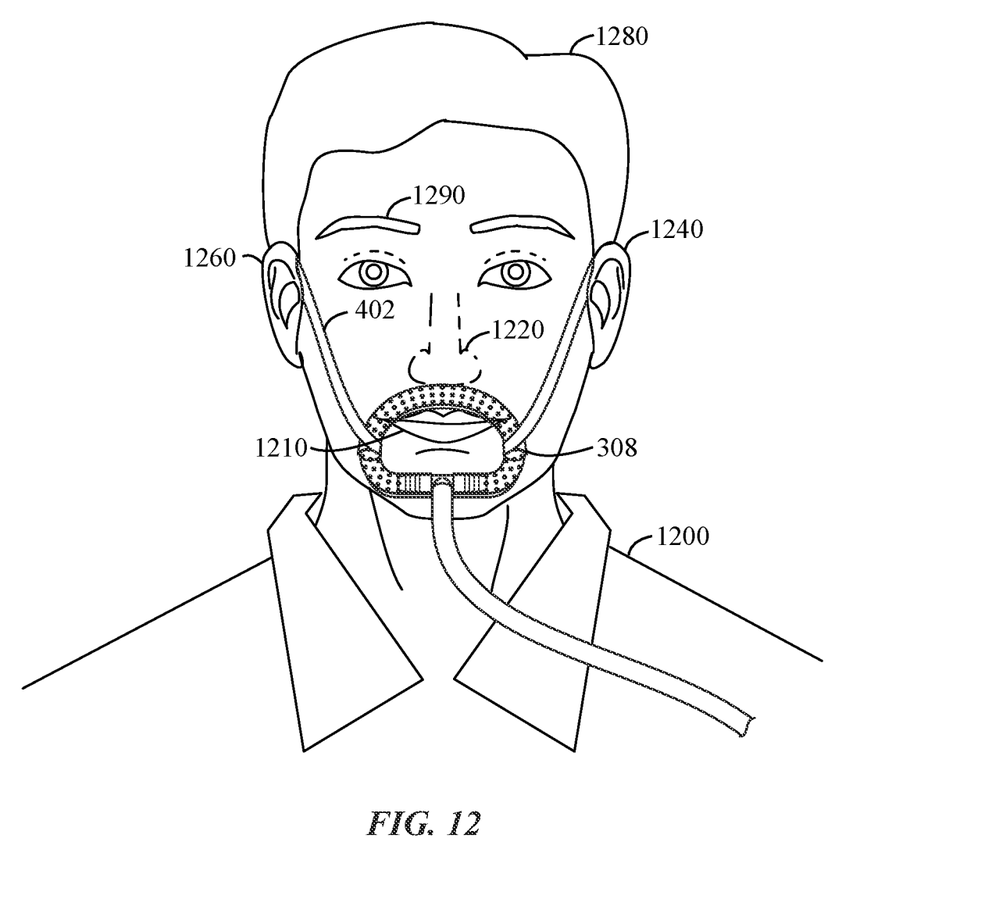
FIG. 12 illustrates a perspective view of the device in an in-use configuration, according to some embodiments.

FIG. 12 illustrates a user 1200 having the device in an in-use position. The flexible tubing 308 is positioned around the mouth 1210 of the user while being positioned under the nostrils and nose 1220 to capture pathogens and contaminants escaping the mouth 1210 and nose 1220. The vacuum tubing 200 extends to a vacuum suction device (not shown) which negatively pressurizes the interior of the flexible tubing 308 to draw air through the plurality of air intake ports 314. The strap 402 extends over the ears 1240, 1260 and around the back of the head 1280 to retain the device 400 on the face 1290 of the user.

While not shown, the vacuum suction device may include known vacuum suction devices commonly used in the arts of dentistry and healthcare. In such, the vacuum tubing 200 may readily connect to known vacuum suction devices.

In some embodiments, the device 400 may be used to capture pathogens and contaminants emitted from non-human sources. For example, the device's 400 dimensions may be modified such that the flexible tubing 308 extends around the opening of a toilet, such that the device 400 is operated when the toilet is flushed to prevent contaminants from escaping the toilet bowl. Similarly, the dimensions of the device 400 may be modified such that the flexible tubing 308 extends around a seating pod to prevent pathogens from escaping the environment wherein a user is seated. In such, the device 400 may not only be used to prevent the spread of pathogens from known infected users, but also as a prophylactic agent which passively operates to remove contaminants and pathogens from the environment.

The device described hereinabove may be packed as a single unit, or in individual components such that the user and/or healthcare professional may readily assemble the device before use. The saliva ejector 1100 is placed into the saliva ejection port 1010 and is positioned to enter the mouth, passing over the lower lip and extending just inside the lower lip of the patient. A protective layer may be provided over the skin adhesive 702 layer, which is removed before application. The nasal target area 1120 is then identified such that the device can be properly oriented during use.

In some embodiments, an optional, provided, removable protective visor may be positioned on the outer surface of the device 400, retained by a retentive fabric (such as Velcro or similar fabric). This protective visor will be retained only on the left, bottom, and right sides of the tube-face and arching upward away from the nose/lips, extending up over the anticipated bridge of the nose to lay passively near/on the skin surface. The protective visor is designed to aid in ambient droplet containment prior to an intra-oral or trans-oral procedure and is temporarily removed by the healthcare professional from the surface of the device 400 during the procedure. Following the procedure, the protective visor is reattached to the retention fabric. The protective visor is constructed of a thin, flexible and optically clear, vacuum formed vinyl/plastic sheet, that allows the healthcare professional observation of lip movement during speaking, an important aid in use for a hearing or speech impaired user or healthcare personnel. Additionally, the removability of the visor serves to provide for a reduction in fear/anxiety often observed in anxiety-laden or claustrophobic users. Additionally, the easy and fast removability of the protective visor permits rapid access to the mouth/lungs during an unexpected emesis (vomiting) event where emergency suction is required to prevent aspiration of gastric contents. The use of the removable visor increases the efficiency of droplet collection by the device 400 directing droplet debris into the suction aspect of device 400 for removal. Device 400 can be used during the simultaneous use of a nasal cannula for introduction of oxygen as required by the patient.

Many different embodiments have been disclosed herein, in connection with the above description and the drawings. It will be understood that it would be unduly repetitious and obfuscating to describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

It will be appreciated by persons skilled in the art that the present embodiment is not limited to what has been particularly shown and described hereinabove. A variety of modifications and variations are possible in light of the above teachings without departing from the following claims.

What is claimed is:

1. A pathogen containment system comprising:
a flexible tubing dimensioned to extend around a user's mouth, the flexible tubing including a first end and a second end;
a connector having a central portion including a first side fittingly engaged with the first end of the flexible tubing and a second side fittingly engaged with the second end of the flexible tubing;
an attachment port in fluid communication with the central portion of the connector and in fluid communication via a vacuum tubing to a vacuum suction unit; and
a plurality of air intake ports provided on the flexible tubing to permit air to be drawn therethrough via the vacuum suction unit, the air intake ports to capture a contaminant emitted from the user's mouth or the user's nose;
wherein the flexible tubing and the connector form a loop dimensioned to extend around a user's mouth when the first side of the connector is fittingly engaged with the first end of the flexible tubing and the second side of the connector is fittingly engaged with the second end of the flexible tubing.

2. The pathogen containment system of claim 1, further comprising at least one pad positioned on a back side of the flexible tubing.

3. The pathogen containment system of claim 1, wherein the at least one pad includes an adhesive to adhere the pad to the user's skin.

4. The pathogen containment system of claim 1, further comprising a strap including a first end having a first retainer and a second end having a second retainer, each attached to the flexible tubing, wherein the strap extends around the user's head.

5. The pathogen containment system of claim 1, further comprising a saliva ejection port positioned on the connector.

6. The pathogen containment system of claim 5, wherein the saliva ejection port is positioned on an opposing side of the attachment port.

7. The pathogen containment system of claim 6, further comprising a plug to cover the saliva ejection port.

8. The pathogen containment system of claim 6, further comprising a saliva ejector attached to the saliva ejection port.

9. The pathogen containment system of claim 8, wherein the saliva ejector extends into the user's mouth.

10. A pathogen containment system comprising:
a flexible tubing dimensioned to extend around a user's mouth, the flexible tubing including a first end and a second end each engaged with a connector having a central portion including a first side fittingly engaged with the first end of the flexible tubing and a second side fittingly engaged with the second end of the flexible tubing the flexible tubing comprising a nasal target area to properly orient the flexible tubing on the user's face;
an attachment port in fluid communication with the central portion of the connector and in fluid communication via a vacuum tubing to a vacuum suction unit to provide negative pressure to the flexible tubing;
a plurality of air intake ports provided on the flexible tubing to permit air to be drawn therethrough via the vacuum suction unit, the air intake ports to capture a contaminant emitted from the user's mouth or the user's nose; and a strap connected to the flexible tubing to retain the device on the user's face;

wherein the flexible tubing and the connector form a loop dimensioned to extend around a user's mouth when the first side of the connector is fittingly engaged with the first end of the flexible tubing and the second side of the connector is fittingly engaged with the second end of the flexible tubing.

11. The pathogen containment system of claim 10, a first pad arranged at a top of the flexible tubing and a second pad positioned at a bottom of the flexible tubing.

12. The pathogen containment system of claim 11, wherein the strap includes a first end having a first retainer and a second end having a second retainer, each attached to the flexible tubing between the first pad and the second pad, wherein the strap extends around the user's head.

13. The pathogen containment system of claim 12, further comprising a saliva ejection port positioned on the connector.

14. The pathogen containment system of claim 13, wherein the saliva ejection port is positioned on an opposing side of the attachment port.

15. The pathogen containment system of claim 14, further comprising a plug to cover the saliva ejection port.

16. The pathogen containment system of claim 15, further comprising a saliva ejector attached to the saliva ejection port, wherein the saliva ejector extends into the user's mouth.

17. The pathogen containment system of claim 16, further comprising a protective plastic visor positioned on the device to create a chamber above the user's nose and mouth.

18. The pathogen containment system of claim 17, further comprising a plurality of distenders each engaged with each of the plurality of intake ports.

19. The pathogen containment system of claim 18, wherein each of the plurality of distenders include one or more retention lips to prevent the distender from being drawn through each of the plurality of intake ports.

20. A pathogen containment system for use during healthcare procedures, comprising:

a flexible tubing dimensioned to extend around a user's mouth, the flexible tubing including a first end and a second end each engaged with a connector having a central portion including a first side fittingly engaged with the first end of the flexible tubing and a second side fittingly engaged with the second end of the flexible tubing the flexible tubing comprising a nasal target area to properly orient the flexible tubing on the user's face;

an attachment port positioned perpendicular to the central portion, the attachment port in fluid communication via a vacuum tubing to a vacuum suction unit to provide negative pressure to the flexible tubing;

a saliva ejection port opposite the attachment port, the saliva ejection port to receive saliva from the user's mouth, wherein the saliva ejection port is releasably engaged to a saliva ejector extending into the user's mouth;

a plurality of intake ports provided on the flexible tubing to permit air to be drawn therethrough via the vacuum suction unit, the air intake ports to capture a contaminant emitted from the user's mouth or the user's nose; and a strap connected to the flexible tubing to retain the device on the user's face.

\* \* \* \* \*